United States Patent [19]
Cheung

[11] Patent Number: 5,269,768
[45] Date of Patent: Dec. 14, 1993

[54] VALVED SUCTION CATHETER

[75] Inventor: Victor Cheung, Arlington, Mass.

[73] Assignee: Smiths Industries Medical Systems, Inc., Keene, N.H.

[21] Appl. No.: 14,733

[22] Filed: Feb. 8, 1993

[51] Int. Cl.[5] .................................. A61M 5/00
[52] U.S. Cl. .............................. 604/248; 604/119
[58] Field of Search ............ 604/32, 33, 119, 248, 604/249, 902; 433/95

[56] References Cited

U.S. PATENT DOCUMENTS

| | | | |
|---|---|---|---|
| 3,191,600 | 6/1965 | Everett | 604/902 |
| 3,911,919 | 10/1975 | Raitto | 137/625.4 |
| 4,468,216 | 8/1984 | Muto | 604/43 |
| 4,502,508 | 3/1985 | Lester | 137/625.69 |
| 4,526,573 | 7/1985 | Lester et al. | 604/33 |
| 4,569,344 | 2/1986 | Palmer | 128/207.16 |
| 4,680,026 | 7/1987 | Weightman et al. | 604/33 |
| 4,775,365 | 10/1988 | Swartz | 604/248 |
| 4,784,649 | 11/1988 | Imonti et al. | 604/119 |
| 4,966,551 | 10/1990 | Betush | 604/32 |
| 5,019,054 | 5/1991 | Clement et al. | 604/32 |
| 5,203,769 | 4/1993 | Clement et al. | 604/32 |

Primary Examiner—John D. Yasko
Assistant Examiner—Anthony Gutowski
Attorney, Agent, or Firm—Pollock, Vande Sande & Priddy

[57] ABSTRACT

A closed system suction catheter assembly has a valve which controls suction applied at the patient end of the assembly. The valve has a barrel with a bore through it which is rotatable in a housing between an open position, in which the bore is aligned the inlet and outlet of the valve and a closed position, in which it is out of alignment. The barrel has teeth on its outer surface forming a pinion which are engaged by teeth on the underside of a slidable switch. Sliding of the switch rotates the barrel and controls flow through the valve.

9 Claims, 2 Drawing Sheets

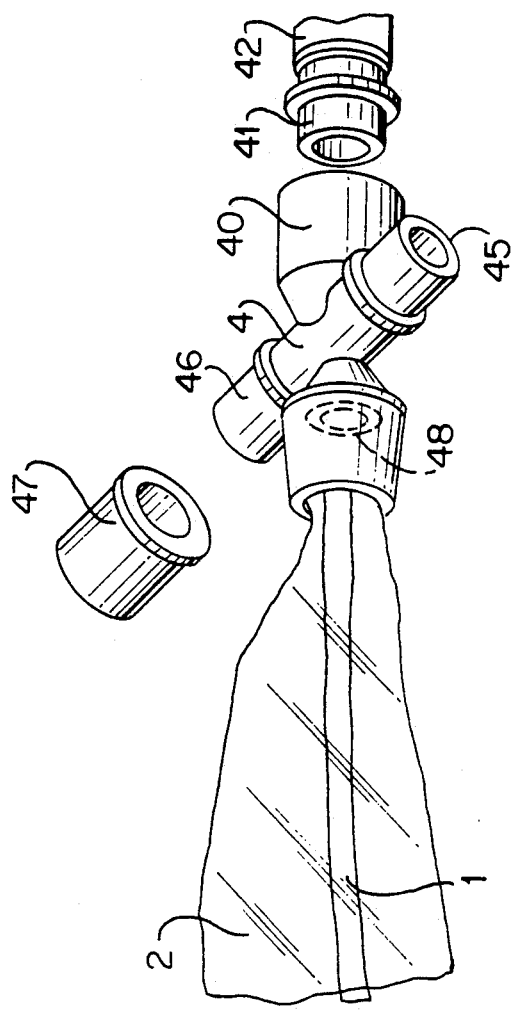
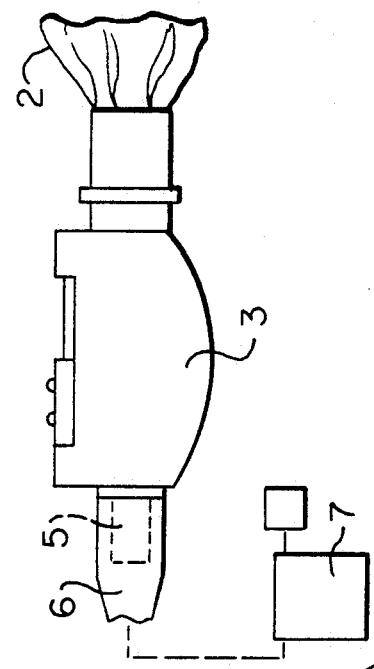
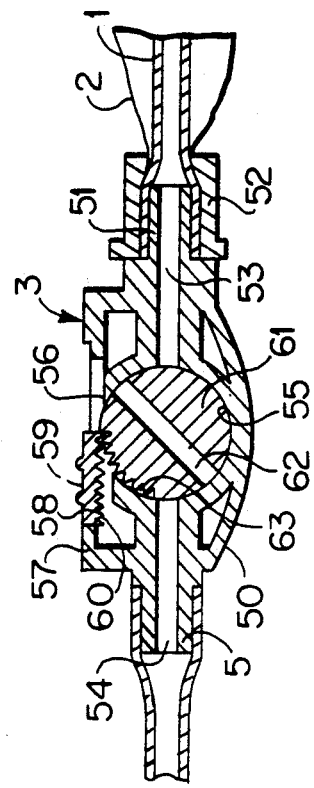
FIG. 1
FIG. 2
FIG. 3

VALVED SUCTION CATHETER

BACKGROUND OF THE INVENTION

This invention relates to suction catheter assemblies and valves.

The invention is more particularly concerned with medical suction catheter assemblies including valves which can be used for aspirating secretions from the respiratory system or tracheal tubes or, for example, for removing blood and debris from surgical sites.

Suction catheter assemblies of this kind are connected to the inlet of a container, the outlet of the container being connected to a vacuum pump so that a reduced pressure is created in the container which in turn applies suction to the catheter. In such systems, the vacuum pump generally operates continuously and the catheter includes a valve by which suction at the tip of the catheter can be controlled. In its simplest form, the valve comprises an aperture in the wall of the catheter which, when open, allows air to enter the catheter and thereby prevents any significant suction effect at the tip. The aperture can be closed, when desired, by the thumb of the user, or by a movable flap, so that the suction effect is confined to the tip of the catheter.

Examples of such catheters are described in U.S. Pat. Nos. 3,911,919 and 4,468,216. The problem with this form of valve is that the suction control aperture provides a path through which contaminated material sucked into the catheter can leak out. This is a significant disadvantage in view of the present concern about cross-infection and the transmission of infectious diseases.

In order to reduce the risk of escape of material, catheters have been made which include a sealed valve. Examples of suction catheters with a push-down spool valve are shown in U.S. Pat. Nos. 4,680,026, 4,526,573 and 4,502,508. A suction catheter with a resilient valve member is described in U.S. Pat. No. 4,569,344. Many other forms of suction catheter with different suction control valves are also known.

One problem with these valves is that they have as a part of their sealing system an obstruction to flow. The obstruction is created by the stem which connects the spool, plunger or other seal to the manually-actuable button by which the valve is operated. In some valves the stem itself creates the seal. The obstruction created by the stem causes the fluid flow path to be split into two paths around opposite sides of the stem. This does not permit the free flow of thick fluids, such as thick respiratory fluids.

BRIEF SUMMARY OF THE PRESENT INVENTION

It is an object of the present invention to provide a suction catheter assembly and valve that can be used to alleviate the above-mentioned problems.

According to one aspect of the present invention there is provided a suction catheter assembly comprising a suction catheter and a valve connected to the catheter to control flow of fluid along the catheter, the valve comprising: a housing, the housing having an inlet and an outlet; a valve member having a fluid passageway therethrough; means mounting the valve member with the housing for rotatable movement about an axis transverse to the fluid passageway; a manually-actuable member; means mounting the manually-actuable member for linear movement relative to the housing along a path transverse to the axis of rotation of the valve member, the valve member and the manually-actuable member having contacting surfaces such that displacement of the manually-actuable member effects rotation of the valve member, and the manually-actuable member being movable from a first position, in which the fluid passageway through the valve member is aligned with the inlet and outlet of the housing so that fluid can flow through the valve, to a second position, in which the fluid passageway is out of alignment with at least one of the inlet and outlet so that fluid is prevented from flowing through the valve.

The contacting surfaces preferably each have teeth that engage each other. The teeth may be provided by a rack on the manually-actuable member and by a pinion on the valve member. The pinion may be formed around a circumference of the valve member or may be a pinion gear at one end of the valve member. The inlet and outlet are preferably axially aligned, the manually-actuable member being movable either parallel to or transversely of the axis of the inlet and outlet. The manually-actuable member may include a thumb pad at one end such that by pushing down on the thumb pad the manually-actuable member is moved down and transversely of the axis of the inlet and outlet.

According to another aspect of the present invention there is provided a suction catheter assembly comprising a suction catheter and a valve connected to the catheter to control flow of fluid along the catheter, the valve comprising: a housing, the housing having an inlet, an outlet and a recess of circular section, the inlet and outlet opening into opposite sides of the recess; a valve member, the valve member being of circular section and having a fluid passageway extending diametrically therethrough; means mounting the valve member in said recess for rotatable movement about an axis transverse to the fluid passageway; a manually-actuable member; means mounting the manually-actuable member for linear movement relative to the housing along a path transverse to the axis of rotation of the valve member, the valve member and the manually-actuable member having respective contacting surfaces such that displacement of the manually-actuable member effects rotation of the valve member, and the manually-actuable member being movable from a first position, in which the fluid passageway through the valve member is aligned with the inlet and outlet of the housing so that fluid can flow through the valve, to a second position, in which the fluid passageway is out of alignment with both inlet and outlet so that fluid is prevented from flowing through the valve.

A suction catheter assembly according to the present invention, will now be described, by way of example, with reference to the accompanying drawings.

BRIEF DESCRIPTION OF THE DRAWINGS

FIG. 1 is a perspective view of the assembly;

FIG. 2 is a plan view from above of the valve of the assembly;

FIGS. 3 and 4 are sectional side elevations of the valve in a closed and an open state respectively;

DESCRIPTION OF THE PREFERRED EMBODIMENTS

Figure 4:
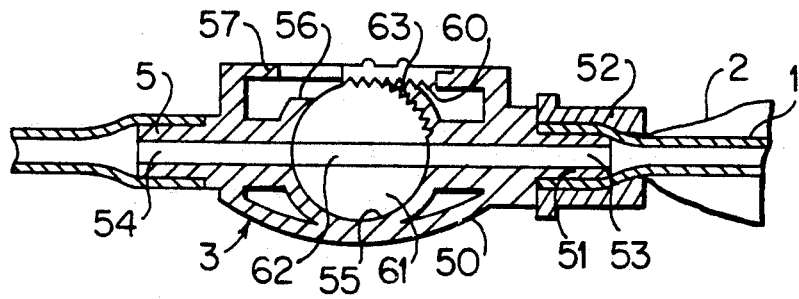

With reference first to FIG. 1, the suction catheter assembly comprises an aspirating catheter 1 that extends within a flexible, protective sleeve 2 between a valve assembly 3 and a patient connecting member 4.

The aspirating catheter 1 is of conventional construction having an outside diameter of about 4-5 mm and a length of about 55 cm. At its machine or proximal end, the catheter 1 is secured to the valve assembly 3.

The valve assembly 3 has a fluid passageway extending along it which communicates at one end with the catheter 1 and at the other end with an outlet spigot 5. In use, the spigot 5 is connected to tubing 6 which extends to a suction source 7. The valve 3 normally prevents flow through the catheter 1 but can be manually actuated by the user to open and connect the lumen of the catheter to the suction source 7.

The patient connecting member 4 is of generally cruciform shape. At its distal, or patient end, the connecting member 4 has a female luer coupling 40 which is aligned with the axis of the member. The coupling 40 is adapted to be connected to a cooperating coupling 41 on the end of a tracheal tube 42. Two sides ports 45 and 46 extend at right angles to the axis of the connecting member, directly opposite one another, about midway along the length of the connecting member. These two side ports 45 and 46 communicate directly with the interior of the coupling 40 and are used in the conventional manner to connect with ventilation apparatus. One port may be used for inhalation gas and the other port used for exhalation gas. Alternatively, one of the ports 46 may be closed by a cap 47 and inhalation and exhalation both be effected through the other port 45.

The patient connecting member 4 also includes a sliding seal 48 in the form of a resilient disc or diaphragm with a central aperture through which the catheter 1 extends as a sliding fit.

With reference now also to FIGS. 2 to 4, the valve assembly 3 has a housing 50 from which the outlet spigot 5 projects at its left-hand end. At its opposite end, the housing has an inlet spigot 51 to which the catheter 1 is joined. The sleeve 2 is also joined to the inlet spigot 51 on top of the catheter 1 by means of an external collar 52. The inlet and outlet spigots 51 and 5 have respective bores 53 and 54 extending along them which are axially aligned with one another. The two bores 53 and 54 open into opposite sides of a cylindrical recess 55 the axis of which extends transversely, at right angles to the two bores. The recess 55 has an opening 56 at its upper end which lies just beneath a support structure 57. The support structure 57 extends axially of the housing 50 and transversely of the recess 55; the structure serves to support a sliding switch or manually-actuable member 58 which can be slid linearly along a part of the length of the housing. The upper surface 59 of the switch 58 is ribbed so that it can be gripped by the clinician's finger or thumb; the lower surface of the switch is shaped to form a rack 60 the teeth of which contact and engage a valve member 61.

The valve member 61 is of a cylindrical or barrel shape, with a circular section, and is located in the recess 55 so that it extends axially of the recess and transversely of the axis of the bores 53 and 54. A fluid passageway 62 extends diametrically across the valve member 61 midway along its length, the diameter of the passageway being the same as that of the bores 53 and 54. Externally, the valve member 61 has a smooth surface apart from a pinion portion 63 provided by teeth which extend around about 80° of its circumference in a central region along the length of the valve member 61. The pinion 63 is exposed through the opening 56 in the recess 55 and is contacted and engaged by the rack 60 on the underside of the switch 58. The valve member 61 is a close fit within the recess 55, so that there is no leakage of fluid between the outside of the valve member and the recess, the valve member being freely rotatable about its axis within the recess by actuation of the switch 58.

In the position shown in FIGS. 2 and 3, the switch 58 is at the right hand end of its support 57 and the valve member 61 is in a counter clockwise position with its fluid passageway 62 inclined at about 45° to the horizontal, so that the passageway is out of alignment with the inlet 53 and outlet 54 of the valve 3. In this position, therefore, the valve is closed and no fluid can flow along the catheter 1. The valve 3 preferably includes a spring (not shown) which engages the valve member 61 and urges it in a counter-clockwise sense, to a closed position.

To open the valve 3, the switch 59 is gripped and pushed to the right, to its full extent, so that it slides linearly along the valve, parallel to the axis of the inlet and outlet bores 53 and 54. The linear movement of the switch 58 is converted to rotational, clockwise movement of the valve member 61 by the rolling, geared engagement of the switch. In this position, (shown in FIG. 4) the fluid passageway 62 lies horizontal and is aligned with both the inlet and outlet bores 53 and 54, so that fluid can flow along the valve through the valve member 61 and suction is applied to the catheter 1. When the switch 58 is released, the spring rotates the valve member 61 in a counter-clockwise sense and displaces the switch to the left, back to the position shown in FIG. 3.

In its open position, the valve 3 provides a smooth, continuous flow path between the inlet and outlet without obstructions, so that there is little risk of blockage. The use of a sliding switch 58 separate from the valve member 61 helps to reduce the risk of contamination that might otherwise occur, if the external surface of the valve member were contacted directly. The valve can be easily held and operated in one hand.

In operation, the coupling 40 of the patient connecting member 4 is secured to the coupling 41 on the end of the tracheal tube 42 and its side ports 45 and 46 are connected to a ventilator. The valve 3 is connected to the suction source 7 but, as long as the valve 3 remains unactuated, no suction is applied to the catheter 1.

When aspiration of fluid from the trachea or bronchi is required, the user grips the catheter 1 through the sleeve 2 and pushes it forwardly so that the distal, patient end of the catheter is advanced through the connecting member 4 and the sliding seal 48 and into the tracheal tube 42. When the catheter 1 has been inserted to the desired depth, the user slides forwards the switch 58 so that the valve 3 opens and the catheter is connected to the suction source 7. Fluid in the vicinity of the tip of the catheter is then sucked into the catheter and removed. During aspiration, ventilation of the patient occurs normally. When aspiration is complete, the catheter 1 is pulled back into the sleeve 2, the assembly remaining attached to the tracheal tube connector 41 so that it can be reused when necessary.

Figure 5:
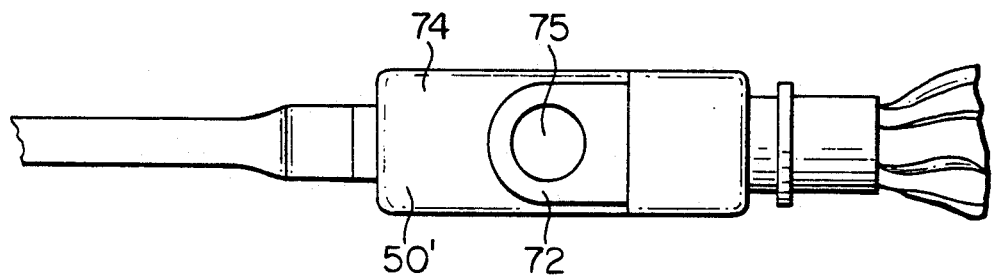
FIG. 5 is a plan view from above of an alternative valve.
Figure 6:
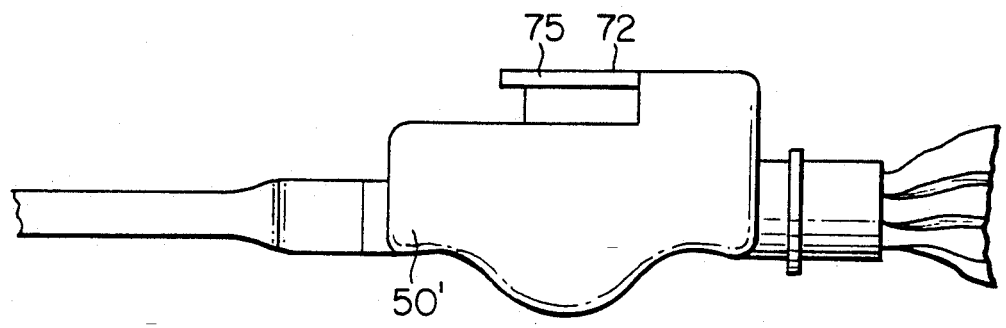
FIG. 6 is a side elevation view of the valve of FIG. 6.
Figure 7:
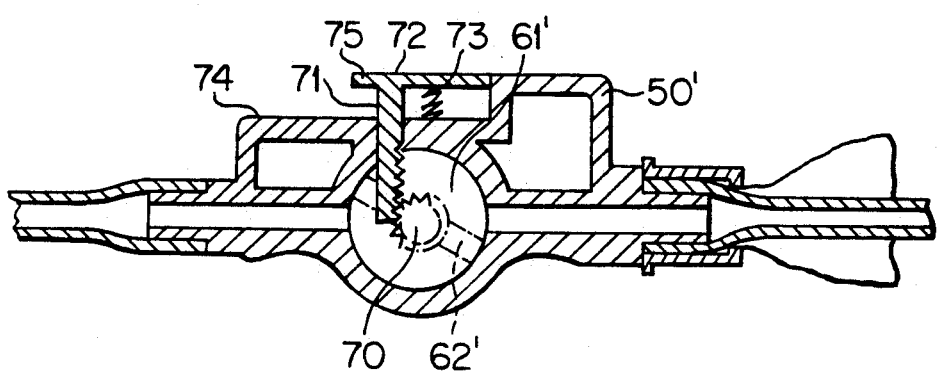
FIG. 7 is a sectional side elevation of the valve in FIGS. 6 and 7.

There are various other ways in which the valve member could be moved between a closed and an open position. One of these alternatives is illustrated in FIGS. 5 to 7. In this arrangement, the valve member 61' has a small pinion gear 70 at one end which is engaged by a vertically-oriented rack 71 on a switch 72. The switch 72 is urged upwardly by a spring 73 lying between an upper surface 74 of the valve housing 50' and the underside of a thumb pad 75. The valve member 61' is urged in a clockwise sense by the switch 72 and its passageway 62' lies at about 30° to the horizontal, that is, out of alignment with the inlet and outlet of the valve, so that the valve is closed. The valve is opened by pushing down on the thumb pad 75, so that the switch 72 slides linearly down against the action of the spring 73 and the valve member 61' is rotated in a counter-clockwise sense, until its passageway 62' is in alignment with the inlet and outlet of the valve.

It is not essential for the switch and valve member to have teeth, since a rolling engagement, in which linear movement of the switch is converted to rotational movement of the valve member, could be achieved by other means, such as, for example, by frictional engagement.

What we claim is:

1. A suction catheter assembly comprising a suction catheter and a valve connected to the catheter to control flow of fluid along the catheter, the valve comprising: a housing, the housing having an inlet and an outlet; a valve member having a fluid passageway therethrough; means mounting the valve member with the housing for rotatable movement about an axis transverse to the fluid passageway; a manually-actuable member; means mounting the manually-actuable member for linear movement relative to the housing along a path transverse to the axis of rotation of the valve member, wherein the valve member and the manually-actuable member have respective contacting surfaces such that displacement of the manually-actuable member effects rotation of the valve member, and wherein the manually-actuable member is movable from a first position, in which the fluid passageway through the valve member is aligned with the inlet and outlet of the housing so that fluid can flow through the valve, to a second position, in which the fluid passageway is out of alignment with at least one of the inlet and outlet so that fluid is prevented from flowing through the valve.

2. A suction catheter assembly according to claim 1, wherein the contacting surfaces each have teeth that engage each other.

3. A suction catheter assembly according to claim 2, wherein the teeth are provided on a rack on the manually-actuable member and by a pinion on the valve member.

4. A suction catheter assembly according to claim 3, wherein the pinion is formed around a circumference of the valve member.

5. A suction catheter assembly according to claim 3, wherein the pinion is a pinion gear at one end of the valve member.

6. A suction catheter assembly according to claim 1, wherein the said inlet and outlet are axially aligned, and wherein the manually-actuable member is movable parallel to the axis of the inlet and outlet.

7. A suction catheter assembly according to claim 1, wherein the said inlet and outlet are axially aligned, and wherein the manually-actuable member is movable transversely of the axis of the inlet and outlet.

8. A suction catheter assembly according to claim 7, wherein the manually-actuable member includes a thumb pad at one end such that by pushing down on the thumb pad the manually-actuable member is moved down and transversely of the axis of the inlet and outlet.

9. A suction catheter assembly comprising a suction catheter and a valve connected to the catheter to control flow of fluid along the catheter, the valve comprising: a housing, the housing having an inlet, an outlet and a recess of circular section, the inlet and outlet opening into opposite sides of the recess; a valve member, the valve member being of circular section and having a fluid passageway extending diametrically therethrough; means mounting the valve member in said recess for rotatable movement about an axis transverse to the fluid passageway; a manually-actuable member; means mounting the manually-actuable member for linear movement relative to the housing along a path transverse to the axis of rotation of the valve member, wherein the valve member and the manually-actuable member have respective contacting surfaces such that displacement of the manually-actuable member effects rotation of the valve member, and wherein the manually-actuable member is movable from a first position, in which the fluid passageway through the valve member is aligned with the inlet and outlet of the housing so that fluid can flow through the valve, to a second position, in which the fluid passageway is out of alignment with both inlet and outlet so that fluid is prevented from flowing through the valve.

* * * * *